(12) United States Patent
Månsson et al.

(10) Patent No.: US 7,863,056 B2
(45) Date of Patent: Jan. 4, 2011

(54) COATED METAL SURFACE ON SOLID SUPPORT FOR ANALYTE DETECTION BY DISPLACEMENT

(75) Inventors: Per Månsson, Sollentuna (SE);
Ann-Sofie Johansson, Västerås (SE);
Björn Sandén, Stockholm (SE); Shahin Loniakan, Kista (SE)

(73) Assignee: Biosensor Applications Sweden AB (SE)

( * ) Notice: Subject to any disclaimer, the term of this patent is extended or adjusted under 35 U.S.C. 154(b) by 1279 days.

(21) Appl. No.: 10/517,322

(22) PCT Filed: Jun. 18, 2003

(86) PCT No.: PCT/SE03/01036
§ 371 (c)(1),
(2), (4) Date: Dec. 15, 2005

(87) PCT Pub. No.: WO04/001416
PCT Pub. Date: Dec. 31, 2003

(65) Prior Publication Data
US 2006/0105471 A1  May 18, 2006

Related U.S. Application Data

(60) Provisional application No. 60/389,496, filed on Jun. 19, 2002.

(30) Foreign Application Priority Data
Jun. 19, 2002 (SE) .................................. 0201875

(51) Int. Cl.
*G01N 33/543* (2006.01)
(52) U.S. Cl. ........................ 436/518; 436/524; 436/525; 436/164; 436/172; 435/283.1; 435/287.1; 435/287.2

(58) Field of Classification Search ................. 436/518, 436/524, 525, 164, 172; 435/283.1, 287.1, 435/287.2
See application file for complete search history.

(56) References Cited

U.S. PATENT DOCUMENTS 5,631,172 A * 5/1997 Johnson ...................... 436/543
(Continued)

FOREIGN PATENT DOCUMENTS

| WO | WO 99/27368 | 6/1999 |
| WO | WO 00/43774 | 7/2000 |

OTHER PUBLICATIONS

Go Sakai et al., "A surface plasmon resonance-based immunosensor for highly sensitive detection of morphine", Sensors and Actuators B, vol. 49, 1998, pp. 5-12.

(Continued)

*Primary Examiner*—Melanie J. Yu
(74) *Attorney, Agent, or Firm*—Bacon & Thomas PLLC

(57) ABSTRACT

A coated metal surface on a solid support, wherein the coating consists of a protein layer firmly attached to the metal surface, and said protein layer is coupled to linker molecules that are bound to low molecular weight antigens, wherein the linker molecules are coupled to the protein layer and are bound to the antigen via functional end groups and contain between the functional end groups an aliphatic hydrocarbon of 1, 2 or 3 carbon atoms, and wherein the antigens are optionally reversibly bound to antibodies specific for the antigens, is described. The coated metal surface on a solid support may be used in a method of detecting analyte antigens as part of an analysis device, such as a Piezoelectric Crystal Microbalance device or a Surface Plasmon Resonance biosensor, for detection in an aqueous solution of an analyte antigen with higher affinity to an antibody than the antigen of the coating by monitoring the displacement of the antibody from the coating.

17 Claims, 6 Drawing Sheets

U.S. PATENT DOCUMENTS

| | | |
|---|---|---|
| 6,294,391 B1 | 9/2001 | Badley et al. |
| 6,905,816 B2 * | 6/2005 | Jacobs et al. .................. 435/5 |
| 2002/0009812 A1 | 1/2002 | Miura et al. |
| 2002/0022588 A1 * | 2/2002 | Wilkie et al. .................. 514/2 |
| 2002/0121314 A1 * | 9/2002 | Tao et al. .................. 148/251 |
| 2003/0162987 A1 * | 8/2003 | Houser et al. .............. 556/431 |
| 2006/0127278 A1 * | 6/2006 | Gast et al. ............... 422/82.05 |

OTHER PUBLICATIONS

Go Sakai et al., "Highly selective and sensitive SPR immunosensor for detection of methamphetamine", Electrochimica Acta, vol. 44, 1999, pp. 3849-3854.

Miura Norio et al., "Drug detection apparatus", Chemical Abstracts, vol. 129, Aug. 21, 1998, Heisei, 13 pp., Abstract No. 223026, (Columbus Ohio, USA), & Jpn. Kokai Tokkyo Koho, JP10221249, A2.

* cited by examiner

Cannabinol

Tetrahydrocannabinol (THC)

Cocaine

Cocaine-linker molecule 2,4,6-Trinitrotoluene (TNT)　　　2,4-Dinitrotoluene (2,4-DNT)

COATED METAL SURFACE ON SOLID SUPPORT FOR ANALYTE DETECTION BY DISPLACEMENT

CROSS REFERENCE TO RELATED APPLICATIONS

This application claims benefit under 35 U.S.C. 119(e) of U.S. Provisional Patent Application Ser. No. 60/389,496 filed Jun. 19, 2002, the whole of which is incorporated herein by reference.

The present invention relates to a coated metal surface on a solid support useful in analyte detection in an aqueous solution by displacement of reversibly bound antibodies specific for the analyte from the metal surface coating. Detection of the displacement, and thus the presence of the analyte in an aqueous solution, is performed with an analysis device, such as a Piezoelectric Crystal Microbalance (PCM) device or a Surface Plasmon Resonance (SPR) biosensor.

BACKGROUND

The SPR biosensor is a sensitive real-time technique, which can be used to extract information about molecular interaction near certain metal surfaces. It offers the possibility to determine concentration, association and dissociation rate constants and affinity as well as epitope mapping and determination of interaction specificity [B. Liedberg and K. Johansen, *Affinity biosensing based on surface plasmon detection* in "Methods in Biotechnology, Vol. 7: Affinity Biosensors: Techniques and Protocols", K. R. Rogers and A. Muchandani (Eds.), Humana Press Inc., Totowa, N.J., pp. 31-53]. One of the components participating in the studied reaction is immobilized on the metal surface either before or during the SPR experiment. The immobilized molecule is exposed to a continuous flow into which one can inject interacting species. The method is based on optical detection and the sensing signal reflects changes in dielectric function or refractive index at the surface. These changes can be caused by molecular interaction at the surface.

The PCM technique is based on an oscillating piezoelectric crystal in a microbalance device, wherein the crystal consists of e.g. quartz, aluminum nitride (AlN) or sodium potassium niobiates (NKN). When the crystal is a quarts crystal, the device is referred to as a QCM (quartz crystal microbalance). The PCM and QCM are gravimetrical sensors and are thus sensitive to mass changes. A QCM comprises a piezoelectric quartz crystal plate upon which metal electrodes have been deposited on both sides. An alternating potential difference applied on such a crystal plate induces shear waves. At certain frequencies—such that the thickness is an odd integer of half wavelengths—the crystal will be in resonance [M. Rodahl, F. Höök, A. Krozer, P. Brzezinski and B. Kasemo, *Quartz crystal microbalance setup for frequency and Q-factor measurements in gaseous and liquid environments*, Review of Scientific Instruments 66 (1995) pp. 3924-3930] and [Saurbrey, Z.Phys. (1959), pp155, 206-222]. The energetically most favourable number of half wavelengths is one. The resonance frequency is dependent on the thickness of the crystal, but is normally in the MHz range. A mass change on the surface of the plate will result in a shift in the resonance frequency. The fact that frequency shifts of 0.01 Hz can be easily measured makes the QCM a sensitive sensor for determining mass variations. A number of patents and other publications describe the use of piezoelectric quartz crystals (QCM) as affinity-based chemical sensors/detectors in e.g. various immuno-assay techniques, and detection of bacteria and virus. In most of these applications the QCM-instrument is used to analyze the weight gain of the crystal after interaction between antibodies and antigens.

The crystal is used as a microbalance to measure very small masses. The thin piezoelectric sensor crystal electrode used in our experiments has gold evaporated on each side. The crystals can be made to oscillate at its resonance frequency by applying an AC-voltage over the electrode. The principle behind the QCM-technique is that the resonant frequency changes when the mass of the crystal changes. By using this method the mass changes in a bio-molecule layer of a crystal can be monitored. Many studies have been reported utilizing the QCM, where the crystal has been coated with a coating that interacts in a specific way with a molecule or particle, e.g. a bacterium, virus, antibody or antigen, resulting in a loss or gain of weight of the crystal, which change in weight is measured.

There are obvious difficulties in analyzing small molecules with conventional immunosensors due to the low response, i.e. small change in weight of the sensor crystal. For attaining the necessary detection of small molecules, the sensitivity of the system has to be improved. This may be achieved by using displacement reactions where a large antibody molecule is detached from the sensor surface by dissociation and reaction with an analyte antigen that has a higher affinity to the antibody than the antigen bound to the sensor surface.(Willner et. al EP 0 843 816).

DESCRIPTION OF THE INVENTION

The present invention provides a coated metal surface on a solid support that is useful in an analysis device for detection of an analyte antigen in an aqueous solution by monitoring displacement of a reversibly bound antibody from the coating by dissociation and reaction with the analyte antigen.

In this specification and claims the word antibody is intended to comprise whole antibodies or antigen-binding parts of antibodies or synthetic antigen-binding molecules.

Thus, one aspect of the invention is directed to a coated metal surface on a solid support, wherein the coating consists of a protein layer firmly attached to the metal surface, and said protein layer is coupled to linker molecules that are bound to low molecular weight antigens, wherein the linker molecules are coupled to the protein layer and are bound to the antigen via functional end groups and contain between the functional end groups an aliphatic hydrocarbon of 1, 2 or 3 carbon atoms, and wherein the antigens are optionally reversibly bound to antibodies specific for the antigens.

The firm attachment of the protein layer to the metal surface may be accomplished by contacting the protein, e.g. albumin, casein, various globulins, LDH, ovalbumin, with the cleaned metal surface whereby the protein adheres to the surface, or the protein may be immobilized onto a pre-deposited functional surface (containing e.g. tiol, carboxylic acid and/or amino groups), or by grafting onto the surface by cross-linking to a polymer structure on the surface.

The linker molecules are coupled to the protein layer by reaction between functional end groups on the linker molecules, such as tiol, carboxylic acid, amino, and hydroxide groups, and functional groups on the protein, such as tiol, carboxylic acid, hydroxyl groups and amino groups.

The linker molecules are usually at first bound to the low molecular weight antigens by reaction between functional end groups on the linker molecules, such as tiol, carboxylic acid, amino and hydroxyl groups or leaving groups, e.g. halides, mesylates, tosylates, activated carboxylic acids, e.g. acid anhydrides and acid chloride, and functional groups on the antigens, such as amino, keto, and hydroxyl groups. It may be necessary to introduce or create a reactive functional group on the low molecular weight antigen prior to the reaction, e.g. in case the antigen lacks functional groups for the reaction.

An important feature of the linker molecule in the coating of the present invention is that it has, in addition to the functional end groups for reaction between the protein layer and the antigen, a short aliphatic hydrocarbon chain of 1, 2 or 3 carbon atoms. If the linker group in the coating is longer than 3 carbons, the affinity to the antibody is too high so that only a limited displacement of the antibody can be monitored upon exposure to the analyte antigen in aqueous solution, which decreases the sensitivity.

The coated metal surface on a solid support according to the invention will usually be stored separately from the antigen-specific antibodies prior to use. When used in displacement analysis, the coated metal surface on a solid support will, however, comprise the specific antibodies reversibly bound to the antigens of the coating.

The metal of the coated metal surface on a solid support according to the invention is preferably selected from the group consisting of gold, silver, aluminum, chromium and titanium. The presently preferred metal is gold.

The antigen of the coating is the same as or a derivative of the analyte antigen except that it is immobilized through a bond to the linker molecule. The antigen of the coating may thus be derivatized to modulate dissociation of the bound antibody in an aqueous solution.

The antigens bound to the linker molecules of the coating according to the invention are the same or different and are bound to the same protein layer or to different patches of protein layers, i.e. the antigens may bind to the same specific antibodies or there may be a mixture of two or more bound antigens binding to different specific antibodies enabling the detection of the presence of several different analyte antigens in an aqueous solution. In case the antibodies carry different markers, such as fluorescent markers, it will be possible to detect displacement of the different antibodies. However, a mixture of several different antibodies will normally be used in cases where screening of samples for any of the target antigens is sufficient, such as screening of samples for any narcotics or explosives. The different antibodies may be kept apart from each other by coating the metal surface with discrete patches or microarrays of spots of proteins carrying different antigens. In a preferred embodiment of the invention the antigen of the coating is selected from the group consisting of optionally derivatized explosives and narcotics. In case the selected antigen of the coating binds too strongly to the specific antibody so that the dissociation of the antibody in aqueous solution is hampered, the antigen molecule may be chemically modified, e.g. by modification of functional groups such as ester or amino groups (by removal of, or replacing the original groups) or by eliminating a part of the antigen molecule, or introducing new functional groups or side chains to the antigen molecule, to reduce its affinity to the antibody.

The explosives are preferably selected from the group consisting of trinitrotoluene (TNT), dinitrotoluene (DNT), hexahydro-1,3,5-trinitro-1,3,5-triazine (RDX), octahydro-1,3,5,7-tetranitro-1,3,5,7-tetrazine (HMX), pentaerythritol tetranitrate (PETN), and nitroglycerine (NG), and the narcotics are preferably selected from the group consisting of cocaine, heroine, amphetamine, methamphetamine, cannabinols, tetrahydrocannabinols (THC), and methylenedioxy-N-methylamphetamine (Ecstacy).

In a presently preferred embodiment the solid support of the coated metal surface on a solid support according to of the invention is a piezoelectric crystal electrode or a glass plate or prism. In case the crystal is a quartz crystal, the coated metal surface on the piezoelectric quarts crystal electrode is suitable for use in a QCM device, whereas the coated metal surface on a glass plate or prism is suitable for use in a SPR apparatus.

Another aspect of the invention is directed to the use of the coated metal surface on a solid support according to the invention as part of an analysis device for detection in an aqueous solution of analyte antigens with higher affinity to specific antibodies than the antigens of the coating by monitoring the displacement of the antibodies from the coating.

Yet another aspect of the invention is directed to a method of detecting analyte antigens in an aqueous solution comprising activating, if necessary, the coated metal surface on a solid support according to the invention lacking bound antibodies by bringing antigen-specific antibodies into contact with the coated metal surface in an aqueous solution, allowing binding of the antibodies to the antigens of the coating, removing excess antibodies, bringing the aqueous solution possibly containing the analyte antigens that have higher affinity to the antibodies than the antigens of the coating into contact with the antibodies reversibly bound to the coating, allowing the antibodies to dissociate and react with the analyte antigens, and detecting the loss of mass on the coated metal surface by means of an analysis device. In an embodiment of the method of the invention the analysis device is selected from the group consisting of a Piezoelectric Crystal Microbalance device and a Surface Plasmon Resonance biosensor. The piezoelectric crystal is e.g. of quarts, aluminum nitride (AlN) or sodium potassium niobiates (NKN).

In a presently preferred embodiment the analysis device comprises a flow cell in which the coated metal surface on a solid support according to the invention is placed.

The invention will now be illustrated by some drawings and description of experiments, but it should be understood that the invention is not intended to be limited to the specifically described details.

GENERAL DESCRIPTION OF EXPERIMENTS

The experiments were conducted in a QCM-system having electrodes optimized to improve the sensitivity of the analysis of low molecular weight compounds. The immunosensing system is based on a principle of displacement.

The immunoassay system that consists of an electrode, which is functionalzed with an antigen derivative immobilized to a gold surface of the electrode via a short linker molecule and a protein layer. Monoclonal antibodies against the antigen was then introduced to the antigen functionalized electrod.

The monoclonal antibodies against the antigen were prepared by immunization of mice with the same antigen linked, by a longer link than the 1-3 carbon atom linker used for the coating of the present invention, to KLH (Keyhole Limpet Hemocyanin). The antibody syntheses procedure is a well-known procedure. [see e.g. Hybridoma Technology in the Biosciences&Medicine. T. A. Springer, editor, Plenum Press, 1985.] The antibodies used in our analysis exhibit sub-nanomolar affinity to the antigen with very defined specificity.

Figure 5:
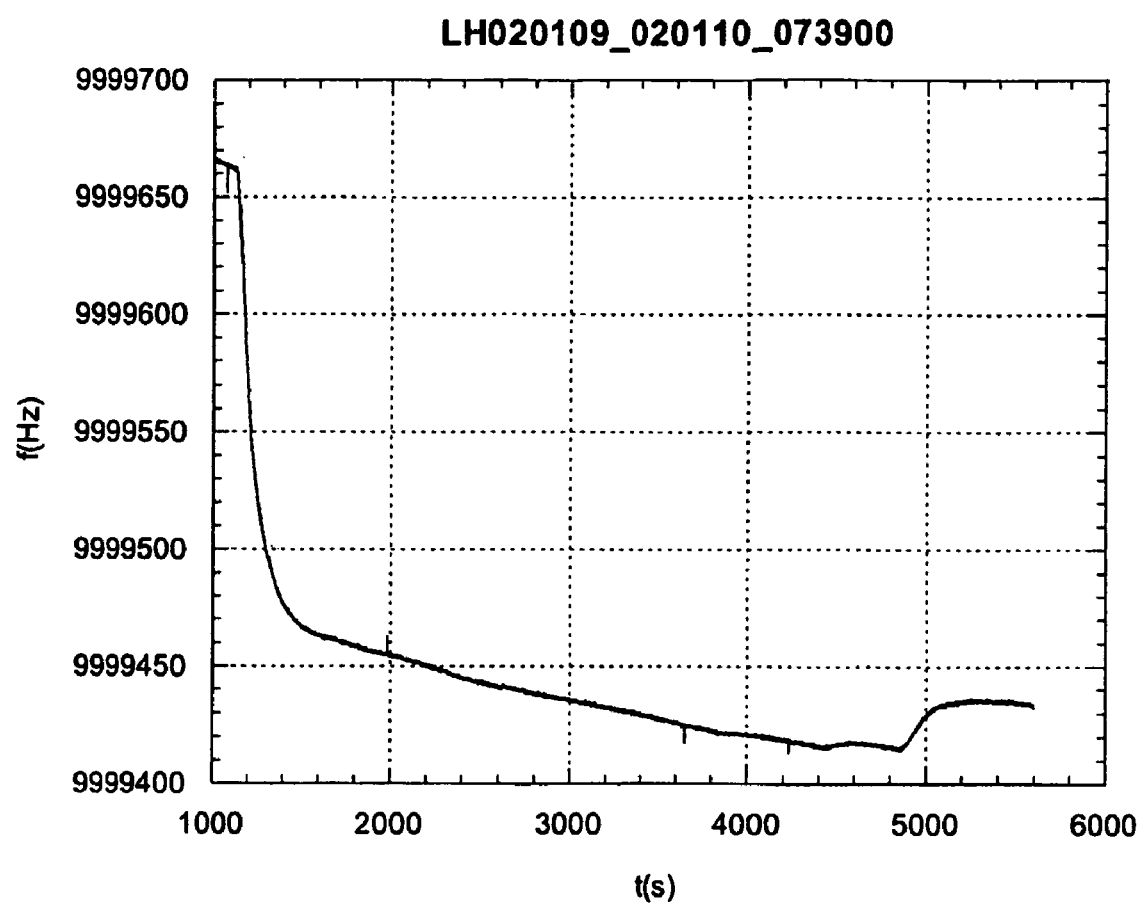
FIG. 5 shows the relative frequency change upon antibody injection against cocaine (0.02 mg/ml) and subsequently injection of cocaine (10 pg/µl). The flow rate is 50 µl/min and the injection volume (loop volume) 100 µl.
Figure 6:
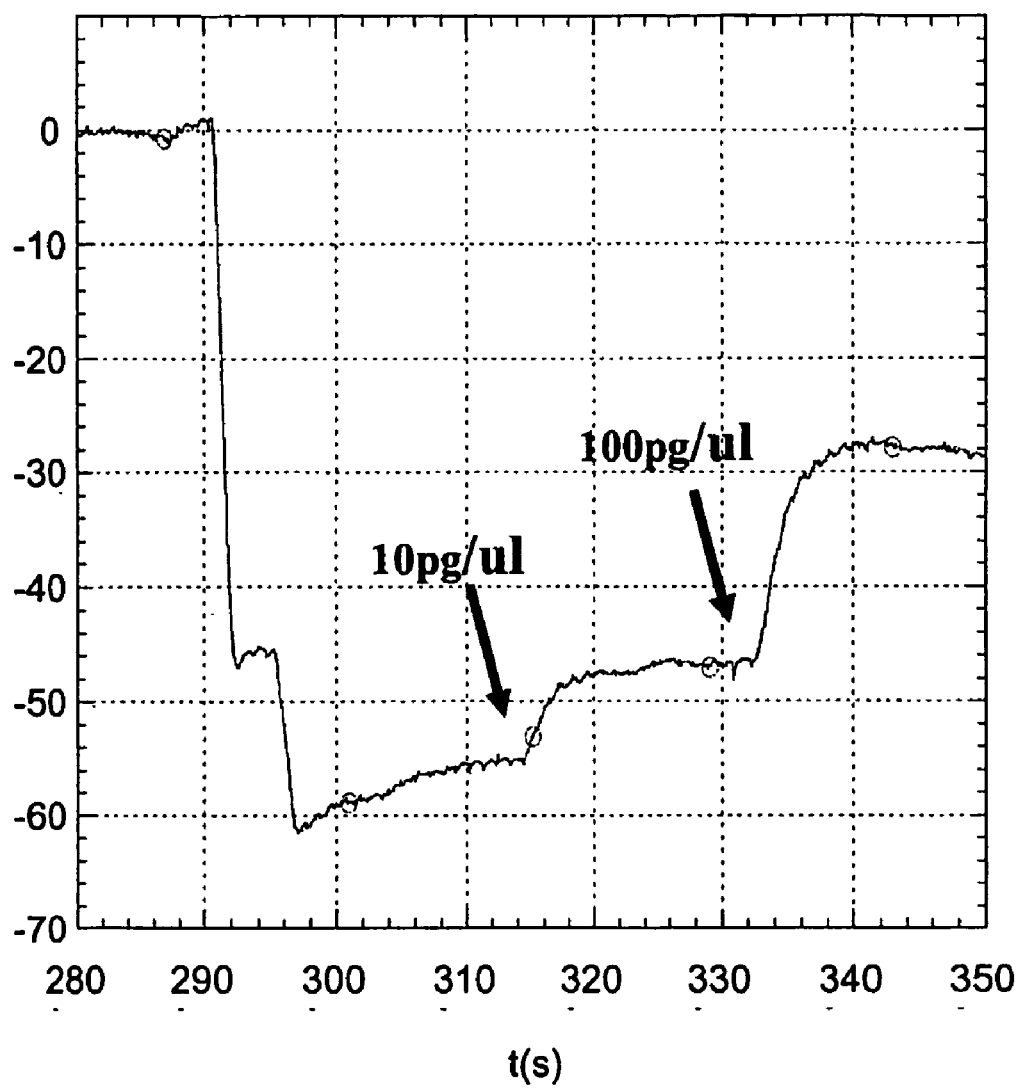
FIG. 6 shows the relative frequency change upon antibody injection and subsequently injection of TNT (10 pg/µl and 100 pg/µl). The flow rate is 250 µl/min.

When the electrode is exposed to the free antigen (analyte) in solution a decrease in weight due to a displacement of the surface bound antibodies can be seen. This decrease in weight of the electrode is monitored by an increase in the oscillation frequency of the crystal (FIGS. 5,6).

Figure 1:
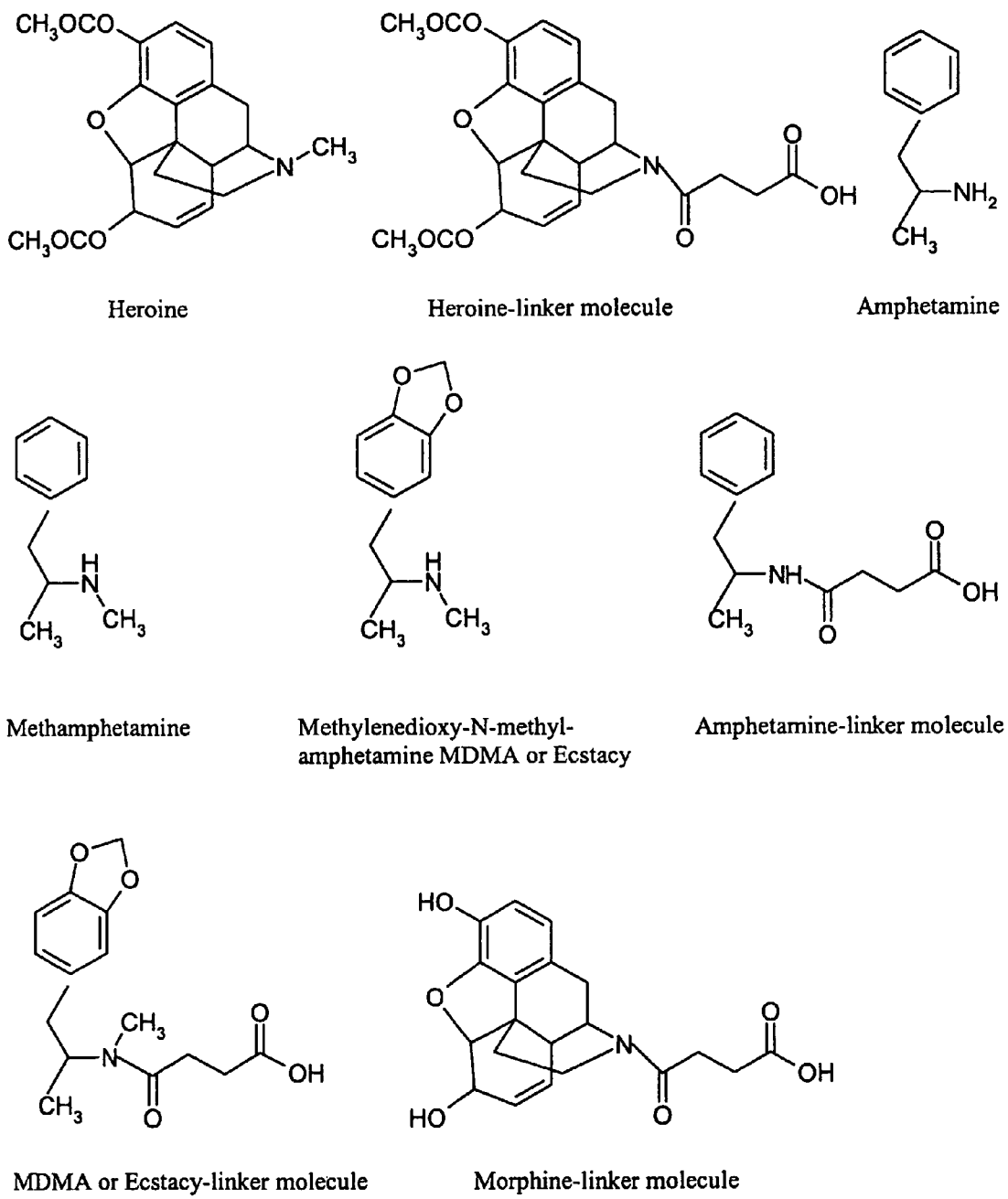
FIG. 1 shows the chemical formula of some narcotics, Heroine, Amphetamine, Ecstacy, and Methamphetamine, and narcotics-linker molecules, Heroine-linker molecule, Amphetemine-linker molecule, Ecstacy-linker molecule and Morphine-linker molecule.
Figure 2:
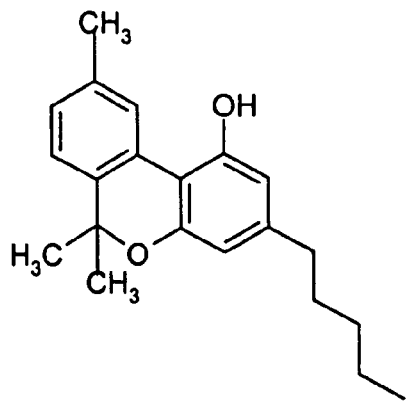
FIG. 2 shows the chemical formula of some additional narcotics, Cannabinol, Tetrahydrocannabinol and Cocaine, and a Cocaine-linker molecule.
Figure 2:
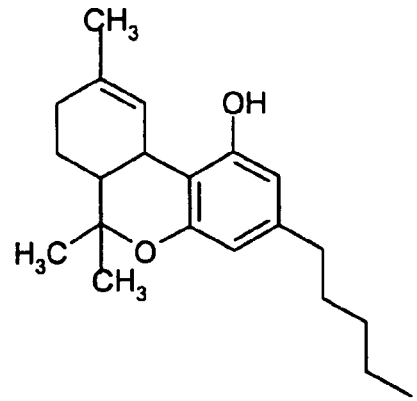
Figure 2:
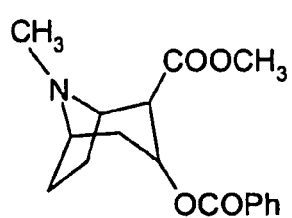
Figure 2:
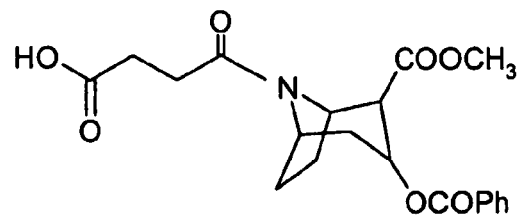
Figure 3:
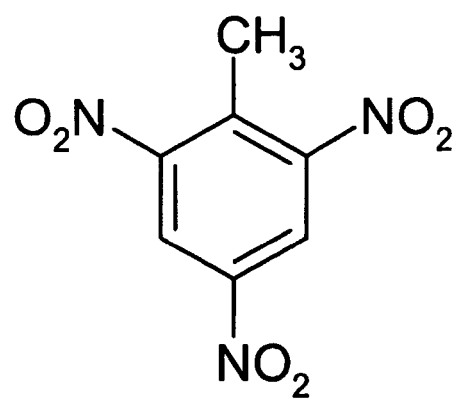
FIG. 3 shows the chemical formula of some explosives, 2,4,6-Trinitrotoluene (TNT) and 2,4-Dinitrotoluene (2,4-DNT).
Figure 3:
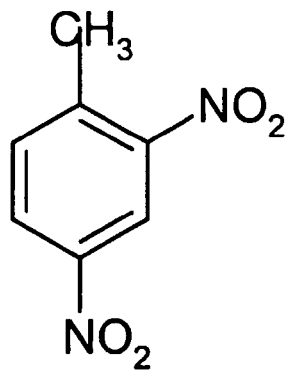
Figure 4:
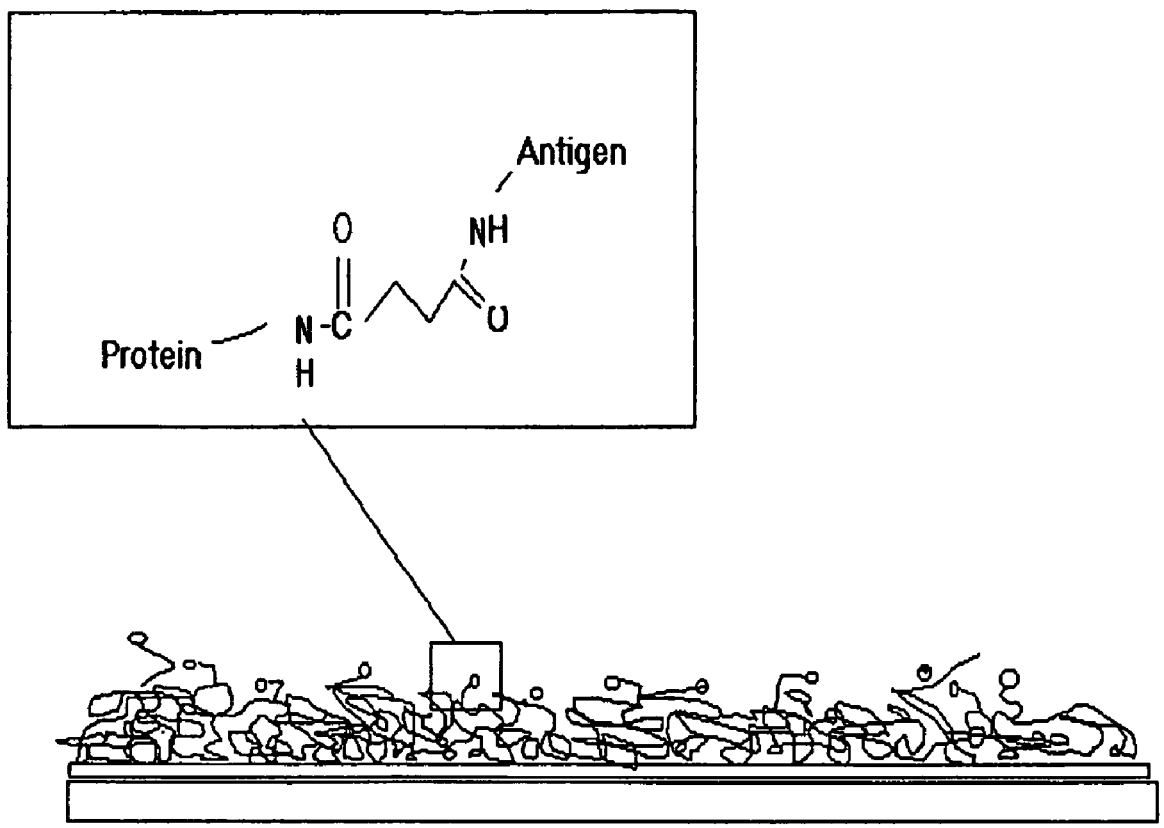
FIG. 4 is a schematic figure showing a typical coating of an antigen-linker molecule conjugated to a protein that is attached to a gold surface. The binding of the antigen via the linker molecule to the protein is highlighted.

In the present experiments the antibodies against the antigens to be detected (analyte antigens) are first physically bound to the surface localized antigen derivatives, i.e. the antigens of the coating of the invention, by weak interactions. When these weakly bound antibody/antigen complexes are exposed to the antigen in solution, the analyte antigen, a fraction of the weakly bound antibodies will leave the surface coating, due to a stronger affinity to the analyte antigen in solution. This will reduce the mass of the QCM-crystal giving an increase of the frequency. The concept is based on the fact that the antibody has a higher affinity to the antigen (analyte) in solution compared to its affinity to the surface localized antigen (high dissociation constant, Kd). It is of utmost importance that the affinity between the antibody and the surface is optimized to give a weight loss upon a contact with a low concentration of the analyte antigen without too much weight loss upon contact with the buffer containing no antigen. It is therefore very important to optimize the affinity of the antibodies to the surface bound antigen.

The trade off in the method is the level of background signal. When a surface bound antibody has too high affinity to the immobilized antigen the displacement of the antibody by free antigen is very difficult and a larger amount of free antigen is needed to displace the antibody from the surface. On the other hand, if the surface bound antibody exhibits too low affinity towards the surface bound antigen the antibody will leave the surface too fast even in the absence of free antigen. The dynamic in the weak biological interaction in such a system is intriguing, binding and release are occurring simultaneously and it is not that easy to predict and optimize a system for technical use in a biosensor.

The quartz crystal electrodes are coated with a metal e.g. gold, which is chemically modified in order to minimize the adsorption of proteins, especially antibodies. In addition, the surface layer is also functionalized with an antigen-derivative which functions as a weak antigen for the antibody of interest. It is very important that no adsorption of other antibodies is occurring (non-specific adsorptions). A number of various surface modifications have been tested to find an antigen-functionalized surface coating, which is protein-repellent (no non-specific adsorption).

We have tested the method by grafting antigen structures relating to trinitrotoluene (TNT), dinitrotoluene (DNT), heroine, amphetamine, methamphetamine, methylenedioxy-N-methylamphetamine (extacy), tetrahydrocannabinol (THC) and cocaine onto various proteins, that were used to modify the electrode surface in the QCM-apparatus. The antigens were grafted on the amino groups on the proteins via a carboxylic acid group on a linker bound to the antigen.

DETAILED DESCRIPTION OF EXPERIMENTS

Conjugation of Cocaine to a Protein e.g. Various Albumins Gamma Globulins, and Other Well Characterized Proteins.

In general we conjugated the antigens to the proteins by using the water soluble carbodiimide EDC [(1-ethyl-3-(3-dimethylaminopropyl) carbodiimide] along with N-hydroxysuccinimide (NHS) to create active ester intermediates of the carboxylated antigen derivatives (e.g. the carboxylated drug-linker molecules in FIGS. 1 and 2). The activated NHS-esters of the antigens were then added to an aqueous solution of the protein, subsequently dialyzed against buffer.

The antigen (20 μmole) was reacted with a 60 μmole NHS and 50 μmole EDC in dimethylformamide (0.5 ml) for 2 h at room temperature. The protein (20 mg) (e.g. albumin) was dissolved in 3 ml 0.1 M $NaHCO_3$, pH 8. The DMF-solution of the activated cocaine was mixed with the protein solution during 4 h at room temperature, subsequently dialyzed against buffer in 24 h.

Coating of QCM-electrodes

The gold surface of the piezoelectric electrode is washed with various solvents and water prior to soaking the electrode in a solution of the protein conjugate (conc. 0.1-3 mg/ml) for 1 h at room temperature, subsequently washed thoroughly in distilled water and allowed to dry.

Measurement Procedure

The coated piezoelectric electrode was fixed in a flow through cell with an internal volume of approximately 10 μl. The cell volume is sealed with a soft rubber O-ring and only one side of the electrode is in contact with the flowing system. The flow rate is adjusted between 5-500 μl/minute (phosphate buffer, PBS). The samples are injected via a loop (50-100 μl) to the cell (flow rate of between 5-500 μl/minute). The reaction (weight gain or weight loss) of the surface modified electrode is continuously monitored as a measurement of the change in frequency.

Results

When injecting an antibody (concentration 0.02 mg/ml, loop volume 0.1 ml) against cocaine a selective adsorption of the antibody immediately occurred resulting in a pronounced decrease in the frequency (see FIG. 5). When a buffer solution continuously is flowing through the cell after the antibody injection, a slight increase of the frequency often is observed, which indicates a slight loss of antibody. However, when injecting a sample of cocaine (concentration of 10 pg/μl and 100 pg/μl, loop volume 0.1 ml) an increase in frequency can be observed.

The same pattern is seen in FIG. 6, when injecting antibody against TNT and injecting TNT-samples.

A series of conjugates between cocaine derivatives, i.e. cocaine bound to linker molecules, and a protein, albumin, were made. One of the cocaine-linker molecules is shown in FIG. 2. Only the derivatives having shorter aliphatic chains than 4 carbon atoms, in addition to possible carbon atoms in the functional end groups (carboxylic acid group in FIG. 2), show a significant displacement of antibody on exposure to the analyte (i.e. cocaine).

Also other cocaine derivatives having long linkers bound to the molecule were tested and resulted in no displacement of the antibody at exposure to the free cocaine in solution. In conclusion, from these experiments it is evident that the affinity between the immobilized cocaine antigen and its antibodies was too high to be useful in the displacement analysis when using long linkers.

Heroine antigens were functionalized in similar way on its OH-groups and N-group. The results clearly showed a pronounced increase in detected displacement when the linker molecule had less than 4 carbon atoms.

Observations made with Final Antigen/Antibody Coated Metal Surfaces of the Invention:
1. Very little non-selective adsorption of antibody compared to the selective antibody.
2. Active in aqueous solution for the displacement reaction for a long time (e.g. >8 h,RT, in a flow cell)
3. Minor desorption (base line drift) of antibody when no analyte is present. (e.g. 0.5%/min in aqueous solution in a flow cell)
4. Stable in dry state when antigen loaded (>3 months at room remperature (RT).

The invention claimed is:

1. A coated metal surface on a solid support, wherein the coating consists of a protein layer firmly attached to the metal surface, and said protein layer is coupled to linker molecules that are bound to low molecular weight antigens, wherein the linker molecules are coupled to the protein layer and are bound to the antigen via functional end groups and contain between the functional end groups an aliphatic hydrocarbon chain of 1, 2 or 3 carbon atoms, and wherein the antigens are reversibly bound to antibodies specific for the antigens.

2. The coated metal surface on a solid support according to claim 1, wherein the metal is selected from the group consisting of gold, silver, aluminum, nickel, chromium and titanium.

3. The coated metal surface on a solid support according to claim 1, wherein the antigens are the same or different and are bound to the same protein layer or to different patches of protein layers and are selected from the group consisting of optionally derivatized explosives and narcotics.

4. The coated metal surface on a solid support according to claim 3, wherein the explosives are selected from the group consisting of trinitrotoluene (TNT), dinitrotoluene (DNT), hexahydro-1,3,5-trinitro-1,3,5-triazine (RDX), octahydro-1,3,5,7- tetranitro-1,3,5,7-tetrazine (HMX), pentaerythritol tetranitrate (PETN), and nitroglycerine (NG).

5. The coated metal surface on a solid support according to claim 3, wherein the narcotics are selected from the group consisting of cocaine, heroineheroin, amphetamine, methamphetamine, cannabiols, tetrahydrocannabiols (THC), and methylenedioxy-N-methylamphetamine (Ecstacy).

6. The coated metal surface on a solid support according to claim 1, wherein the solid support is a piezoelectric crystal electrode or a glass plate or prism.

7. A method of detecting analyte antigens in an aqueous solution comprising activating the coated metal surface on a solid support according to claim 1 lacking bound antibodies by bringing antigen-specific antibodies into contact with the coated metal surface in an aqueous solution, allowing binding of the antibodies to the antigens of the coating, removing excess antibodies, bringing the aqueous solution possibly containing the analyte antigens that have higher affinity to the antibodies than the antigens of the coating into contact with the antibodies reversibly bound to the coating, allowing the antibodies to dissociate and react with the analyte antigens, and detecting the loss of mass on the coated metal surface by means of an analysis device.

8. A method according to claim 7, wherein the analysis device is selected from the group consisting of a Piezoelectric Quartz Crystal Microbalance device and a Surface Plasmon Resonance biosensor.

9. The method according to claim 7, wherein the analysis device comprises a flow cell in which the coated metal surface on a solid support is placed.

10. The method according to claim 8, wherein the analysis device comprises a flow cell in which the coated metal surface on a solid support is placed.

11. A coated metal surface on a solid support, wherein the coating consists of a protein layer firmly attached to the metal surface, wherein the metal is selected from the group consisting of gold, silver, aluminum, nickel, chrome chromium and titanium, and said protein layer is coupled to linker molecules that are bound to low molecular weight antigens, wherein the linker molecules are coupled to the protein layer and are bound to the antigen via functional end groups and contain between the functional end groups an aliphatic hydrocarbon chain of 1, 2 or 3 carbon atoms, and wherein the antigens are reversibly bound to antibodies specific for the antigens.

12. The coated metal surface on a solid support according to claim 11, wherein the antigens are the same or different and are bound to the same protein layer or to different patches of protein layers and are selected from the group consisting of optionally derivatized explosives and narcotics.

13. The coated metal surface on a solid support according to claim 12, wherein the explosives are selected from the group consisting of trinitrotoluene (TNT), dinitrotoluene (DNT), hexahydro-1,3,5-trinitro-1,3,5-triazine (RDX), octahydro-1,3,5,7-tetranitro-1,3,5,7-tetrazine (HMX), pentaerythritol tetranitrate (PSTN), and nitroglycerine (NG).

14. The coated metal surface on a solid support according to claim 12, wherein the narcotics are selected from the group consisting of cocaine, heroine, amphetamine, methamphetamine, cannabiols, tetrahydrocannabiols (THC), and methylenedioxy-N-methylamphetamine (Ecstacy).

15. The coated metal surface on a solid support according to claim 11, wherein the solid support is a piezoelectric crystal electrode or a glass plate or prism, the antibodies are more weakly bound to the immobilized antigens than to an analyte antigen to be tested for by displacement of the antibody from the immobilized antigen.

16. The coated metal surface of clam 15, wherein the antibodies are monoclonal antibodies produced with the same immobilized antigen linked by a longer linker than the 1-3 carbon atom linker for the coating of the coated metal surface to Keyhole Limpet Hemocyanin (KLH).

17. The coated metal surface of claim 16, wherein the antibody has sub-nanomolar affinity to the antigen.

* * * * *